United States Patent
Onitsuka et al.

[11] Patent Number: 6,086,861
[45] Date of Patent: *Jul. 11, 2000

[54] COMPOSITION FOR TREATMENT AND CARE OF HAIR AND SCALP

[75] Inventors: Satoshi Onitsuka, Oyamashi, Japan; Polina Dubowoj, Pfungstadt, Germany

[73] Assignee: KAO Corporation, Japan

[ * ] Notice: This patent is subject to a terminal disclaimer.

[21] Appl. No.: 09/018,715

[22] Filed: Feb. 4, 1998

Related U.S. Application Data

[63] Continuation of application No. 08/638,346, Apr. 26, 1996, Pat. No. 5,716,605.

[30] Foreign Application Priority Data

Apr. 28, 1995 [DE] Germany .................. 195 15 609

[51] Int. Cl.⁷ ..................................................... A61K 7/40
[52] U.S. Cl. ............................................. 424/70.1
[58] Field of Search ............................................. 424/70.1

[56] References Cited

U.S. PATENT DOCUMENTS 5,026,548  6/1991  Evans .
5,152,989  10/1992  Kemp .

FOREIGN PATENT DOCUMENTS 0661047  7/1995  European Pat. Off. .
55-164613  12/1980  Japan .

*Primary Examiner*—Judy M. Reddick
*Attorney, Agent, or Firm*—Londa & Gluck LLP

[57] ABSTRACT

A composition for the treatment and care of hair and scalp, particularly for the treatment of itching, with additional moisturizing and hypoallergenic potential, providing the hair with shine and condition, comprises an aqueous-alcoholic or alcoholic extract of oat seed (Avena sativa), particularly oatmeal, preferably in combination with hydroxycarboxylic acids.

10 Claims, No Drawings

COMPOSITION FOR TREATMENT AND CARE OF HAIR AND SCALP

This application is a continuation of Ser. No. 08/638,346, filed Apr. 26, 1996 issued as U.S. Pat. No. 5,716,605.

BACKGROUND OF THE INVENTION

This invention comprises a composition for the treatment and care of hair and scalp having particularly a reduced itching potential, improved moisturizing and hypoallergenic properties and providing a shining and conditioning action to the hair.

It has been found that a composition combining these properties may be obtained by adding an alcoholic or aqueous alcoholic extract of oat seed as an active ingredient to the usual carrier materials for hair products.

The use of oatmeal in cosmetic compositions is principally already known, cf., e.g., European Patent Application Nos. 619 950 and 620 979. In these publications, special proportions or mixtures thereof with a defined content of proteins, carbohydrates and fat are used.

A survey on the use of oatmeal in cosmetic compositions is given in an article by D. Paton et al. in "Cosmetics and Toiletries", Vol.110 (March 1995), pp. 63 to 64, 66, 68, 70.

SUMMARY OF THE INVENTION

Based on this state of the art, it has now surprisingly been found that compositions for the treatment and care of hair and scalp with improved properties may be obtained, if an alcoholic or aqueous-alcoholic extract of oat seed or oatmeal is added to such compositions. Preferably the extracts are prepared from the fruit of oats of the species Avena sativa.

The oat seed or meal extract used according to the invention has preferably a dry residue of about 0.5% to about 10%, more preferred about 1% to about 5%, particularly about 2% to about 4% by wt., calculated to the total extract.

Alcohols, preferably polyalcohols, particularly propyleneglycol such as 1,3-propyleneglycol and butyleneglycol, especially 1,3-butyleneglycol, alone or preferably in admixture with water, are used as solvents. The proportion of water to alcohol is between about 3:1 to 1:5, preferably 2:1 to 1:2, particularly about 1:1.

The following example describes the production of an extract which may be used according to the invention:

900 g of dried oat seeds (Avena sativa Linne (Gramineae)) were subdivided into six portions of equal weight. The first portion was extracted with 200 g 1,3-butyleneglycol at 70° C. for 8 hours. The second portion was extracted with the extract thus obtained. This procedure was continued until the six portions were extracted in six steps whereby the extracts obtained previously were used as the solvent for the subsequent step. The extract obtained finally is a light to medium yellow liquid of characteristic odor and has the following properties after optional dilution with water:

| | |
|---|---|
| Specific gravity (20° C.) | 1.015 to 1.045 |
| Refractive index: (20° C.) | 1.390 to 1.410 |
| pH-value | 5.0 to 7.0 |
| Water content | 43% to 53% |
| Dry residue | 2.4% to 3.4% |
| Residue of ignition | <0.5% |

The proportion of the oat seed or oatmeal extract in the compositions according to the invention may be from 0.001% to 10%, especially between 0.05% to 10% by wt., calculated to the dry residue of the extract, preferably about 0.1% to 5% by wt., particularly 0.25% to about 2.5% by wt., wherein a proportion between 0.5% and 1.5% by wt. is particularly advantageous.

The compositions according to the invention may be presented in any form of application, e.g. as solutions, emulsions, dispersions, gels, aerosol foams etc., preferably as hair tonics or hair lotions.

The use in customary shampoos and rinses is also possible.

The pH-value of the compositions according to the invention is preferably acidic, i.e. between about 2.5 and 7, more preferred between 3 and 6, particularly between about 4 and about 5.5.

DETAILED DESCRIPTION

According to a preferred embodiment, the compositions of the invention may preferably contain hydroxycarboxylic acids, particularly in a quantity between about 0.05% and 5% by wt., calculated to the total composition, preferably about 0.1% to 2.5% by wt., more preferred 0.25% to 1.0% by wt.

Suitable hydroxycarboxylic acids which may also be present as water-soluble salts are, in particular, citric acid, lactic acid, tartaric acid, malic acid, salicylic acid, glyoxylic acid, glycolic acid and, preferably, also mixtures of all these acids or part thereof.

The principal composition of products for the treatment and care of hair and scalp is basically well-known and described in various monographies; as an example, reference is made to the monography of K. Schrader, "Grundlagen und Rezepturen der Kosmetika", 2nd Ed., (Huthig-Verlag, Heidelberg, 1989), chapter "Haarkosmetika", pp. 661 to 782, particularly the sections on shampoos and hair cleansing compositions (pp. 677–722), after treatments for the hair (pp. 722–737), as well as hair oils and hair tonics (pp. 760–771). The compositions and ingredients described therein may also be used in the compositions according to the invention.

The following Example shall illustrate the production of a composition according to the invention.

| A SCALP LOTION has the following formula: | |
|---|---|
| Oatmeal extract* | 0.50 (% by wt.) |
| Citric acid | 0.15 |
| Lactic acid | 0.05 |
| Tartaric acid | 0.05 |
| Isostearyl lactylate | 0.05 |
| 1,3-Butanediol | 1.00 |
| Allantoin | 0.05 |
| Carbomer | 0.30 |
| Sodium hydroxide | 0.05 |
| Perfume | 0.01 |
| Ethanol | 30.00 |
| Water | @ 100.00 |

*The oatmeal extract had the following properties:

| | |
|---|---|
| Water content | 46% |
| 1,3-Butanediol content | 49% |
| Dry residue | 3% |
| pH-value | 6.0 |
| Residue of ignition | <0.5% |

Using this composition for a scalp treatment eliminated scalp itching and provided the hair with a fine sheen and a light conditioning effect.

After 12 months storage time at 30° C. the product presented no loss of properties nor sedimentation.

An omission of the oatmeal extract resulted in a product which influenced neither scalp itching nor hair sheen positively, and which had no conditioning effect either.

A SHAMPOO has the following formula:

| | |
|---|---|
| Disodium laureth sulfosuccinate | 8.2 (% by wt.) |
| Sodium PEG-4 lauramide carboxylate | 8.0 |
| Cocamidopropylbetaine | 3.0 |
| Decyl glucoside | 2.0 |
| PEG-160 Sorbitan triisostearate | 1.0 |
| PEG-12 | 1.0 |
| Glyceryl caprate | 1.0 |
| PEG-60 Hydrogenated castor oil | 0.5 |
| Polyquaternium-6 | 0.5 |
| Sodium carboxymethyl cocolypropyl amine | 1.0 |
| Perfume | 0.2 |
| Piroctone Olamine | 0.2 |
| Citric acid | 0.1 |
| Oat meal extract (cf. Example for SCALP LOTION) | 0.1 |
| Benzophenone-3 | 0.1 |
| Preservatives, yellow dyestuff (C.I.-No. 15,985) | q.s. |
| Water | @ 100.0 |

A HAIR RINSE composition of the following formula was prepared:

| | |
|---|---|
| Decyl glucoside | 2.0 (% by wt.) |
| Steartrimonium chloride | 0.6 |
| Di-$C_{12}$–$C_{15}$-alkyl dimonium chloride | 0.3 |
| Cetearyl alcohol | 2.0 |
| Oatmeal extract (cf. Example for SCALP LOTION) | 0.1 |
| Dimethicone | 0.4 |
| Benzophenone | 0.1 |
| Perfume | 0.3 |
| Preservative, dyestuffs | q.s. |
| Water | @ 100.0 |

What is claimed is:

1. A method for the topical treatment of hair and scalp comprising the step of applying to the hair or scalp a composition comprising an alcoholic or aqueous-alcoholic extract of oat seeds or oatmeal (Avena sativa).

2. The method according to claim 1, wherein the oat seed or oatmeal extract comprises about 0.001% to about 10% by weight of the total composition, calculated according to the weight of the dry residue of the extract.

3. The method according to claim 2, wherein the oat seed or oatmeal extract comprises about 0.05% to about 10% by weight of the total composition, calculated according to the weight of the dry residue of the extract.

4. The method according to claim 3, wherein the oat seed or oatmeal extract comprises about 0.1% to about 5% by weight of the total composition, calculated according to the weight of the dry residue of the extract.

5. The method according to claim 1, wherein the extract is a water/polyalcohol oat seed or oatmeal extract.

6. The method according to claim 5, wherein the extract is a butyleneglycol and/or propyleneglycol/water oat seed or oatmeal extract.

7. The method according to claim 1, wherein the composition further comprises one or more hydroxycarboxylic acids or the water-soluble salts thereof.

8. The method according to claim 7, wherein the composition comprises about 0.05% to about 5% by weight of the total composition, of at least one hydroxycarboxylic acid or water soluble salt thereof selected from the group consisting of citric acid, lactic acid, tartaric acid, malic acid, salicylic acid, glyoxylic acid and glycolic acid.

9. The method according to claim 1, wherein the composition is characterized by an acidic pH-value.

10. A method for the topical treatment of hair and scalp comprising the step of applying a composition comprising an alcoholic or aqueous/polyalcohol extract of oat seeds or oatmeal (Avena sativa) to the hair and scalp.

* * * * *